United States Patent
Gofman

(10) Patent No.: US 12,303,261 B2
(45) Date of Patent: May 20, 2025

(54) DEVICES, SYSTEMS, AND METHODS FOR MEASURING ANALYTES IN INTERSTITIAL FLUID

(71) Applicant: Ascensia Diabetes Care Holdings AG, Basel (CH)

(72) Inventor: Igor Y. Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 440 days.

(21) Appl. No.: 17/086,222

(22) Filed: Oct. 30, 2020

(65) Prior Publication Data
US 2021/0137426 A1     May 13, 2021

Related U.S. Application Data

(60) Provisional application No. 62/933,308, filed on Nov. 8, 2019.

(51) Int. Cl.
    *A61B 5/145*         (2006.01)
    *A61B 5/00*          (2006.01)
    *A61B 5/1486*        (2006.01)

(52) U.S. Cl.
    CPC ........ *A61B 5/14532* (2013.01); *A61B 5/1486* (2013.01); *A61B 5/14865* (2013.01); *A61B 5/7221* (2013.01); *A61B 2560/0276* (2013.01)

(58) Field of Classification Search
    CPC .............. A61B 5/14532; A61B 5/1486; A61B 2560/0276; A61B 5/7221; A61B 5/14865;
(Continued)

(56) References Cited

U.S. PATENT DOCUMENTS 5,800,420 A *    9/1998    Gross .................. A61B 5/6848
                                                        600/347
10,201,296 B2     2/2019    Sun et al.
(Continued)

FOREIGN PATENT DOCUMENTS

| CN | 101778594 A | 7/2010 |
|---|---|---|
| CN | 103826528 A | 5/2014 |

(Continued)

OTHER PUBLICATIONS

International Search Report and Written Opinion of International Application No. PCT/EP2020/080920 mailed Apr. 20, 2021.
(Continued)

*Primary Examiner* — David J. McCrosky
(74) *Attorney, Agent, or Firm* — Erise IP, P.A.

(57) ABSTRACT

An analyte monitor includes a controller including a processor coupled to a memory. The memory has instructions stored therein that, when executed by the processor, cause the controller to: provide a working electrode voltage to a working electrode of an analyte sensor; selectively provide a first counter electrode voltage and a second counter electrode voltage to a counter electrode of the analyte sensor; and provide a guard ring voltage to a guard ring associated with the working electrode. The analyte monitor further includes a current measurement circuit coupled to the controller and configured to measure current flow to the working electrode and a reference resistor electrically coupled between the working electrode and the guard ring associated with the working electrode. Other monitors, systems, sensors, and methods are disclosed.

26 Claims, 8 Drawing Sheets

(58) Field of Classification Search
CPC . A61B 5/1451; A61B 5/14514; A61B 5/1459; A61B 5/1468; A61B 5/1473; A61B 5/1495
See application file for complete search history.

(56) References Cited

U.S. PATENT DOCUMENTS

| | | | |
|---|---|---|---|
| 10,231,653 | B2 | 3/2019 | Bohm et al. |
| 2002/0042561 | A1* | 4/2002 | Schulman .......... A61B 5/14532 327/104 |
| 2006/0247508 | A1* | 11/2006 | Fennell .................. G01R 31/52 600/365 |
| 2007/0135697 | A1* | 6/2007 | Reggiardo ......... A61B 5/14865 600/347 |
| 2007/0197889 | A1 | 8/2007 | Brister et al. |
| 2008/0287767 | A1* | 11/2008 | Pasveer .................... A61B 5/25 600/372 |
| 2010/0169035 | A1 | 7/2010 | Liang et al. |
| 2011/0319734 | A1* | 12/2011 | Gottlieb ............. A61B 5/14532 600/347 |
| 2012/0136610 | A1 | 5/2012 | Fennell |
| 2014/0270617 | A1* | 9/2014 | Muller .................. G02F 1/0115 385/3 |
| 2016/0008029 | A1 | 1/2016 | Brister et al. |
| 2016/0157765 | A1 | 6/2016 | Zhu et al. |
| 2019/0117133 | A1 | 4/2019 | Halac et al. |
| 2019/0167167 | A1* | 6/2019 | Mitchell .............. A61B 5/6833 |
| 2020/0245910 | A1* | 8/2020 | Mallas .................. A61B 5/686 |
| 2020/0338351 | A1* | 10/2020 | Panken ................ A61N 1/0534 |

FOREIGN PATENT DOCUMENTS

| | | |
|---|---|---|
| JP | 2009056311 A | 3/2009 |
| JP | 2017051593 A | 3/2017 |
| JP | 2019509865 A | 4/2019 |
| JP | 2019515701 A | 6/2019 |
| TW | 201415404 | 4/2014 |
| TW | 201625925 A | 7/2016 |

OTHER PUBLICATIONS

U.S. Appl. No. 17/334,103, filed May 28, 2021, Hurtz et al.
European Patent Application 20803461.1 Examination Report issued Oct. 16, 2023.
Taiwan Patent Application 109138155 Official Letter and Search Report issued Jan. 25, 2024.
Taiwan Patent Application Decision of Patent Examination Notice of Allowance issued Jun. 12, 2024.
European Patent Application 20803461.1, Intent to Grant issued Apr. 4, 2024.
European Patent Application 21183929.5 Decision to Grant issued Aug. 1, 2024.
Japanese Patent Application 2022-524021, Office Action, issued Aug. 27, 2024.
European Patent Application 24196204.2 Extended Search Report issued Dec. 12, 2024.
Taiwan Patent Application Office Action issued Feb. 11, 2025.
Chinese Patent Application 202080074847.8, Office Action and Search Report, issued Mar. 14, 2025.

* cited by examiner ained by the scope of the claims.

DEVICES, SYSTEMS, AND METHODS FOR MEASURING ANALYTES IN INTERSTITIAL FLUID

CROSS REFERENCE TO RELATED APPLICATION

This claims the benefit of U.S. Provisional Patent Application No. 62/933,308, filed Nov. 8, 2019, and titled "DEVICES, SYSTEMS, AND METHODS FOR MEASURING ANALYTES IN INTERSTITIAL FLUID", the disclosure of which is hereby incorporated herein by reference in its entirety for all purposes.

FIELD

The present disclosure relates to devices, systems, and methods adapted to measure analytes in interstitial fluid.

BACKGROUND

Continuous analyte sensing in an in-vivo and/or in-vitro sample, such as continuous glucose monitoring (CGM), has become a routine sensing operation, particularly in diabetes care. By providing real-time glucose concentrations, therapeutic/clinical actions may be applied more timely and the glycemic condition may be better controlled.

During a CGM operation, a biosensor is typically inserted subcutaneously and is continuously operated in an environment surrounded by tissue and interstitial fluid. The biosensor inserted under the skin provides a signal to a wireless CGM transmitter of the CGM sensor apparatus, and that signal is indicative of the user's blood glucose level. These measurements may be made automatically many times throughout the day (e.g., every few minutes or at some other interval).

The wireless CGM transmitter may adhere to the outer surface of a user's skin, such as on the abdomen or the back of the upper arm, while the biosensor is inserted through the skin so as to contact interstitial fluid.

To ensure accurate glucose readings, CGM devices may periodically run a self-test to confirm proper operation of the biosensor and CGM transmitter. Self-test systems may increase the complexity and cost of CGM transmitters by requiring additional switches and other hardware. As such, improved systems, methods, and apparatus for confirming proper operation of CGM transmitters and biosensors are desired.

SUMMARY

According to a first aspect, an analyte monitor is disclosed. The analyte monitor includes a controller that includes a processor coupled to a memory, the memory having instructions stored therein that, when executed by the processor, cause the controller to: provide a working electrode voltage to a working electrode of an analyte sensor; selectively provide a first counter electrode voltage and a second counter electrode voltage to a counter electrode of the analyte sensor; and provide a guard ring voltage to a guard ring that at least partially surrounds a contact region of the working electrode. The analyte monitor also includes a current measurement circuit coupled to the controller that is configured to measure current flow to the working electrode. The analyte monitor further includes a reference resistor electrically coupled between the working electrode and the guard ring. The memory further comprises instructions that, when executed by the processor, cause the controller to perform at least one integrity check by applying the working electrode voltage to the working electrode, applying the first counter electrode voltage or the second counter electrode voltage to the counter electrode, applying the guard ring voltage to the guard ring, and measuring current flow to the working electrode using the current measurement circuit.

According to a second aspect, an analyte monitoring system is disclosed. The analyte monitoring system includes: an analyte sensor having a working electrode and a counter electrode; a guard ring surrounding at least a portion of a contact region of the working electrode; a reference resistor electrically coupled between the working electrode and the guard ring; and an analyte transmitter coupled to the analyte sensor. The analyte transmitter includes a controller that includes a processor coupled to a memory, the memory having instructions stored therein that, when executed by the processor, cause the controller to: provide a working electrode voltage to the working electrode of the analyte sensor; selectively provide a first counter electrode voltage and a second counter electrode voltage to the counter electrode of the analyte sensor; and provide a guard ring voltage to the guard ring. The analyte transmitter also includes a current measurement circuit coupled to the controller and configured to measure current flow to the working electrode. The memory further comprises instructions that, when executed by the processor, cause the controller to perform at least one integrity check by: applying the working electrode voltage to the working electrode, applying the first counter electrode voltage or the second counter electrode voltage to the counter electrode, applying the guard ring voltage to the guard ring, and measuring current flow to the working electrode using the current measurement circuit.

In a third aspect, a method of operating an analyte monitoring system is disclosed. The method includes: providing an analyte sensor having a working electrode and a counter electrode; providing a guard ring surrounding at least a portion of a contact region of the working electrode; providing a reference resistor coupled between the working electrode and the guard ring; applying a working electrode voltage to the working electrode; selectively applying one of a first counter electrode voltage and a second counter electrode voltage to the counter electrode; applying at least a first guard ring voltage to the guard ring; and measuring current flow to the working electrode.

In another aspect, an analyte sensor configured to attach to skin is disclosed. The analyte sensor includes: a working electrode; a guard ring surrounding at least a portion of a contact region of the working electrode; and a reference resistor connected between the working electrode and the guard ring.

Still other aspects, features, and advantages of the present disclosure may be readily apparent from the following description which illustrates a number of example embodiments and implementations. The present disclosure may also be capable of other and different embodiments, and its several details may be modified in various respects, all without departing from the scope thereof. Accordingly, the drawings and descriptions are to be regarded as illustrative in nature, and not as restrictive. The disclosure covers all modifications, equivalents, and alternatives falling within the scope of the claims.

BRIEF DESCRIPTION OF THE DRAWINGS

The drawings, described below, are for illustrative purposes only and are not necessarily drawn to scale. The drawings are not intended to limit the scope of the disclosure in any way. Like numerals are used throughout to denote the same or like elements.

DETAILED DESCRIPTION

Figure 1A:
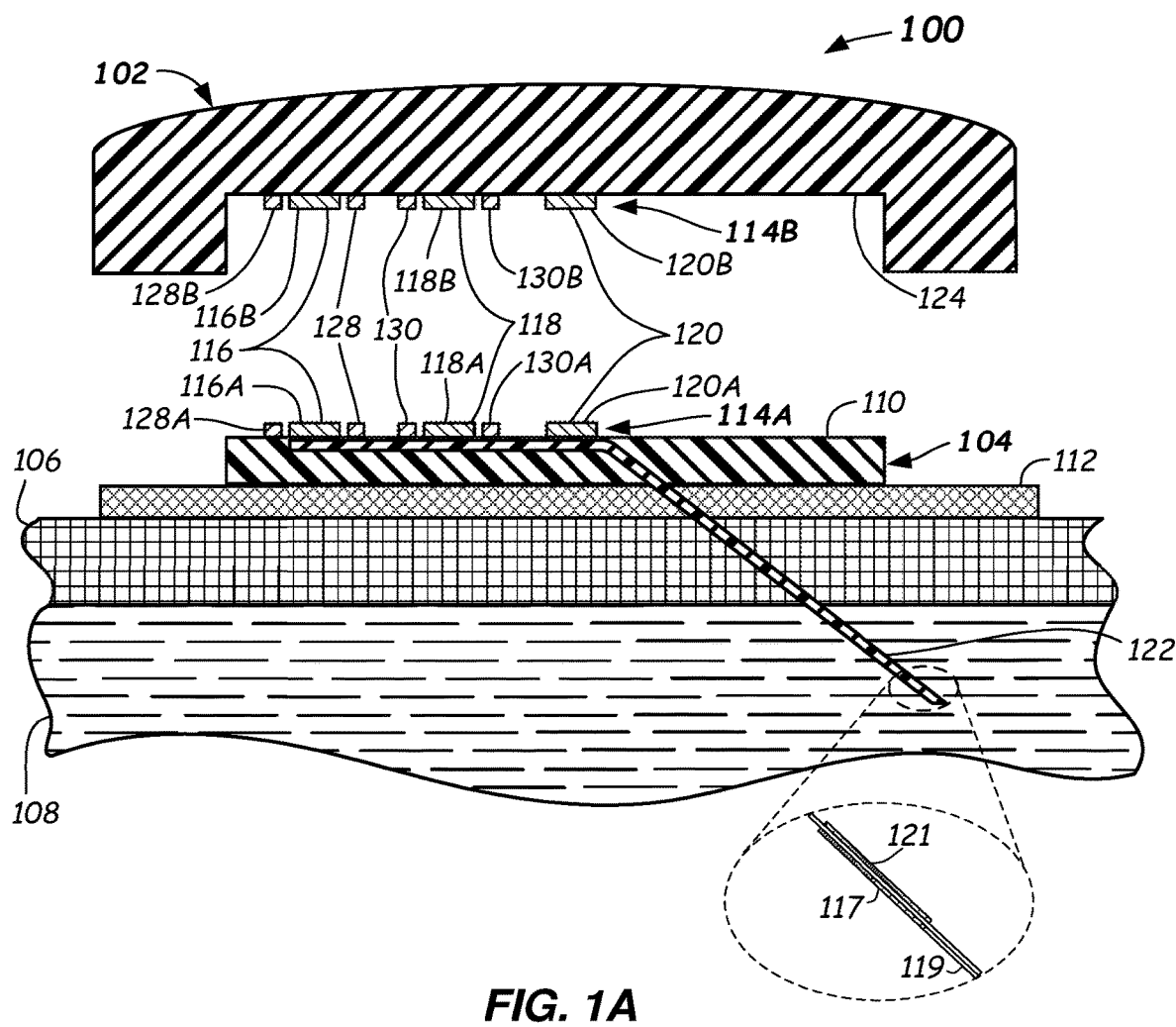
FIG. 1A illustrates a partial, cross-sectioned side view of a glucose monitoring system including a glucose sensor attached to skin and a glucose transmitter shown detached from the glucose sensor according to one or more embodiments.

Continuous analyte monitoring (CAM) systems may monitor current flow between two or more points in interstitial fluid to determine an analyte concentration (e.g., glucose concentration) in the interstitial fluid. A CAM system may include an analyte transmitter electrically coupled to an analyte sensor (e.g., a glucose sensor). The analyte transmitter may include an analog front end having contact regions that electrically couple to contact regions of electrodes of the analyte sensor, such as a working electrode, a counter electrode, a reference electrode and/or the like, which creates electrical connections between the CAM transmitter and the electrodes of the analyte sensor.

The analyte sensor may couple to a baseplate at contact regions of the baseplate. The baseplate may attach to a user's skin, and the analyte transmitter may couple to the baseplate. A needle of the analyte sensor is configured to extend from the baseplate through the user's skin for subcutaneous placement so as to contact interstitial fluid of the user. The needle includes the electrodes of the analyte sensor, such as the working electrode, the counter electrode, and the reference electrode, and places these electrodes into contact with the interstitial fluid below the user's skin. The analyte transmitter and/or baseplate may include one or more guard rings that at least partially surround contact regions of the working electrode and/or the reference electrode of the analyte sensor. For example, a guard ring may surround more than 50% of, and/or substantially surround, a contact region of an electrode in some embodiments.

During CAM, a voltage is applied between the working electrode and the counter electrode and current flow is measured between the electrodes. The current flow between the electrodes is proportional to the analyte (e.g., glucose) concentration in the interstitial fluid. The same voltage applied to the working electrode may be applied to the guard ring associated with the working electrode to prevent current flow through contaminants on the baseplate and/or to prevent the analyte transmitter from interfering with the current measurements through the interstitial fluid. The current flow through the interstitial fluid may be very small, such as in the nanoamperes range, which makes the analyte monitoring system very sensitive. Integrity checks (e.g., self-test routines) may be performed by the CAM system to ensure that the system is operating correctly.

Embodiments of analyte monitoring systems disclosed herein may include a reference resistor electrically coupled between the guard ring (associated with a working electrode) and the working electrode. During a first integrity check, the voltages applied to the working electrode, the guard ring, and the counter electrode are set equal. If the analyte transmitter and/or analyte sensor are operating properly, there should be little or no current flow between the guard ring and the electrodes because they are all at the same voltage. Any current flow or current flow above a predetermined (e.g., threshold) amperage may indicate a fault in the analyte monitoring system (e.g., due to an electrical connection error or contamination of the analyte transmitter, baseplate or sensor).

During a second integrity check, voltages applied to the working electrode and the counter electrode may be equal, while a voltage applied to the guard ring may be different than the voltage applied to the working electrode. If the analyte transmitter and/or analyte sensor are operating properly, little or no current should flow between the working electrode and the counter electrode. Current should flow, however, between the guard ring and the working electrode solely through the reference resistor. The magnitude of the current flow should equal the difference in voltage between the working electrode and the guard ring divided by the resistance of the reference resistor. If other current flow is measured, a fault may be present in the analyte monitoring system (e.g., due to an electrical connection error or contamination of the analyte transmitter, baseplate or sensor).

These and other embodiments are described in detail with reference to FIGS. 1A-8 herein. While described primarily with regard to glucose concentration determinations using glucose monitoring systems, embodiments described herein may also be used with other analyte monitoring systems (e.g., cholesterol, lactate, uric acid, alcohol, or other analyte monitoring systems).

Figure 1B:
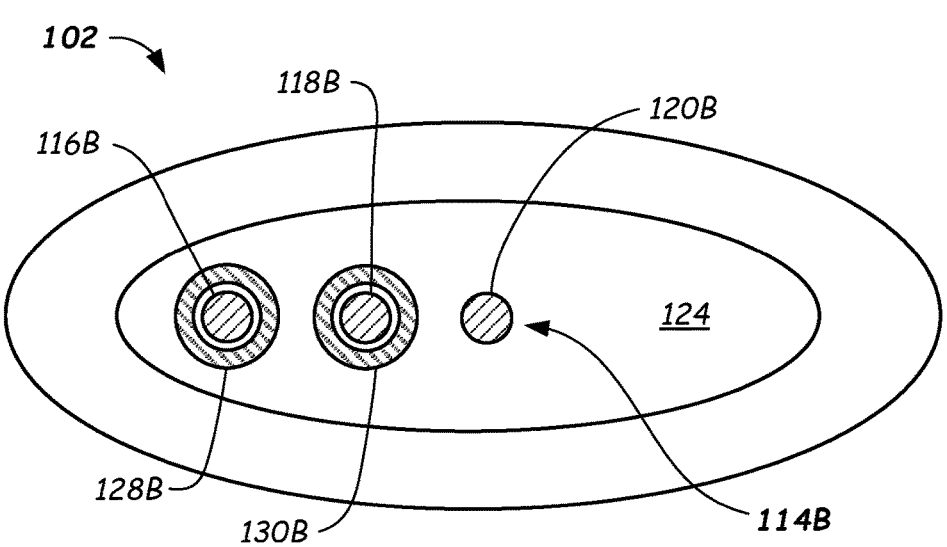
FIG. 1B illustrates a bottom plan view of a glucose transmitter according to one or more embodiments.

Reference is now made to FIG. 1A, which illustrates a partial, cross-sectioned side view of a glucose monitoring system 100 including a glucose transmitter 102 and a glucose sensor assembly 104. The glucose transmitter 102 is shown detached from the glucose sensor assembly 104 to show various features described below, and the glucose sensor assembly 104 is shown attached to skin 106. Reference is also made to FIG. 1B, which illustrates a bottom plan view of an embodiment of the glucose transmitter 102. Interstitial fluid 108 is located beneath the skin 106. The components of the glucose monitoring system 100 and the skin 106 may not be drawn to scale. The glucose sensor assembly 104 may include a substrate 110 (e.g., a base plate)

on which components of the glucose sensor assembly 104 are located. Portions of the substrate 110 may be made of non-conductive materials such as plastic, ceramic or another suitable material. In some embodiments, the substrate 110 may include a laminate material. The substrate 110 may include electrical traces (not shown) that conduct current to components within or attached to the substrate 110. An adhesive 112, such as an acrylic, silicone or the like, may attach the substrate 110 to an outer surface of the skin 106.

In the embodiment of FIGS. 1A-1B, the glucose sensor assembly 104 may include sensor electrode contact regions 114A that include a working electrode contact region 116A, a reference electrode contact region 118A, and a counter electrode contact region 120A for contacting a working electrode 117, a reference electrode 119 and a counter electrode 121, respectively, as described further below. Fewer or more electrode contact regions and/or electrodes, and/or other suitable electrode configurations, may be used. For example, in some embodiments, a second working electrode (e.g., a background electrode) may be employed. The electrodes 117, 119 and 121 may form and/or may be encased within a needle 122 that is configured to be located at least partially beneath the skin 106 in the interstitial fluid 108 so that the electrodes 117, 119 and 121 may contact the interstitial fluid and conduct current to sensor electrodes contact regions 116A, 118A, and 120A.

The glucose transmitter 102 may include a surface 124 on which transmitter contact regions 114B are located. The transmitter contact regions 114B may include corresponding individual contact regions as the sensor electrode contact regions 114A. For example, the transmitter contact regions 114B may include a working electrode contact region 116B, a reference electrode contact region 118B, and a counter electrode contact region 120B. The individual contact regions of the sensor electrode contact regions 114A and the transmitter contact regions 114B may have any shape, such as round, elliptical, square, and rectangular.

In addition to the above-described contact regions, the glucose transmitter 102 and/or the glucose sensor assembly 104 may have guard rings that at least partially surround at least one of the contact regions. In the embodiment depicted in FIGS. 1A and 1B, the glucose sensor assembly 104 includes a working electrode guard ring 128A that surrounds at least a portion of the working electrode contact region 116A. The glucose sensor assembly 104 may also include a reference electrode guard ring 130A that surrounds at least a portion of the reference electrode contact region 118A. The glucose transmitter 102 may include a working electrode guard ring 128B that at surrounds at least a portion of the working electrode contact region 116B and a reference electrode guard ring 130B that surrounds at least a portion of the reference electrode contact region 118B.

Figure 1C:
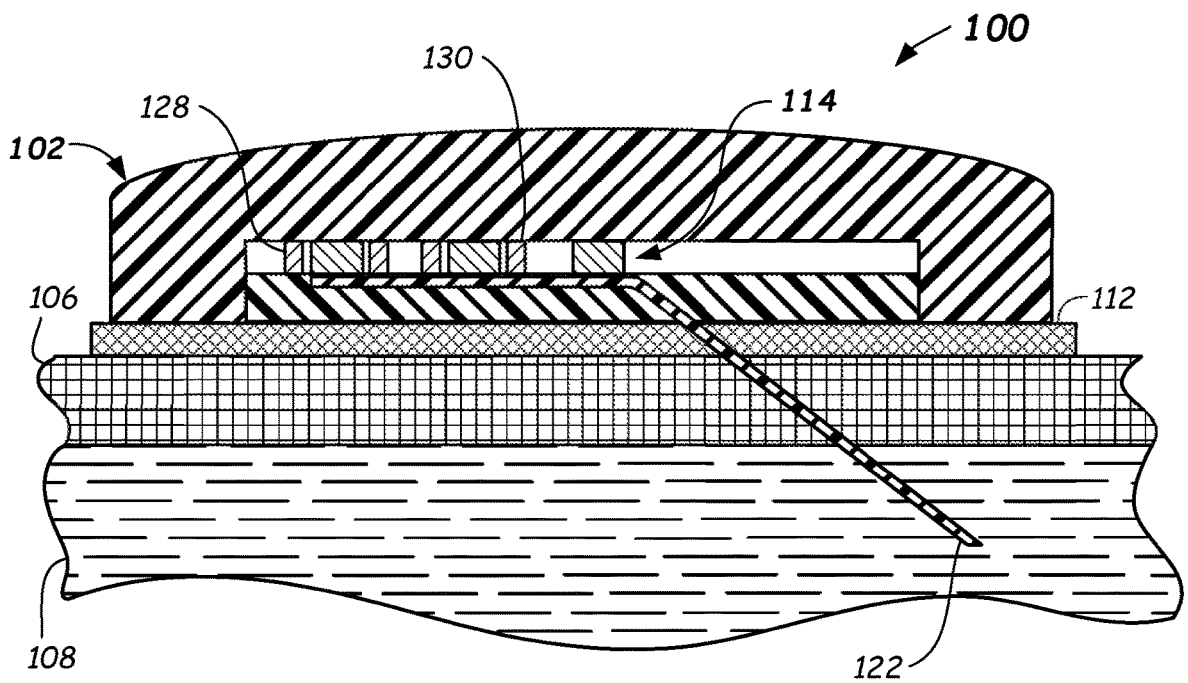
FIG. 1C illustrates a partial, cross-sectioned side view of a glucose monitoring system with a glucose sensor attached to a glucose transmitter according to one or more embodiments.

During operation of the glucose monitoring system 100, the glucose transmitter 102 and the glucose sensor assembly 104 may be attached together as shown in FIG. 1C so that the transmitter contact regions 114B electrically contact the sensor electrode contact regions 114A. The guard rings in the glucose transmitter 102 may also electrically contact respective guard rings in the glucose sensor assembly 104. When the glucose sensor assembly 104 is attached to the glucose transmitter 102, the working electrode contact region 116A and the working electrode contact region 116B may be in electrical contact with working electrode 117, the reference electrode contact region 118A and the reference electrode contact region 118B may be in electrical contact with reference electrode 119, and the counter electrode contact region 120A and the counter electrode contact region 120B may be in electrical contact with counter electrode 121. In addition, the working electrode guard ring 128A and the working electrode guard ring 128B may form a guard ring 128 and the reference electrode guard ring 130A and the reference electrode guard ring 130B may form a guard ring 130. The sensor electrode contact regions 114A and the transmitter contact regions 114B may be referred to collectively as the electrode contact regions 114. In some embodiments, the guard ring 128 and/or the guard ring 130 may have an annular shape. In some embodiments at least one of the guard ring 128 and/or the guard ring 130 may have a round, elliptical, rectangular, or any other suitable shape.

The electrodes 117, 119 and 121 may apply voltages and/or conduct current through the interstitial fluid 108 via the needle 122. For example, during operation of the glucose monitoring system 100, current may flow between the working electrode 117 and the counter electrode 121. The reference electrode 119 may have no or very little current flow and may function to set the voltage of the counter electrode 121. As described herein, the current flow between the working electrode 117 and the counter electrode 121 is proportional to the concentration of glucose in the interstitial fluid 108. Thus, the glucose monitoring system 100 may measure the current flow between the working electrode 117 and the counter electrode 121 to determine the glucose concentration in the interstitial fluid 108.

The guard ring 128 prevents stray current from flowing on the surface 124 of glucose transmitter 102 and/or the surface of the substrate 110 and from being interpreted as current flow through the interstitial fluid 108. The guard ring 128 may include a conductive ring that surrounds at least a portion of the working electrode contact region 116 and may contact the surface 124. During operation of the glucose sensor assembly 104, the guard ring 128 may be operated at the same voltage as the working electrode 117. Because the guard ring 128 and the working electrode 117 operate at the same voltage, there should be no current flow between the working electrode 117 and the guard ring 128. Therefore, only current flowing through the interstitial fluid 108 flows through the working electrode 117.

Figure 2:
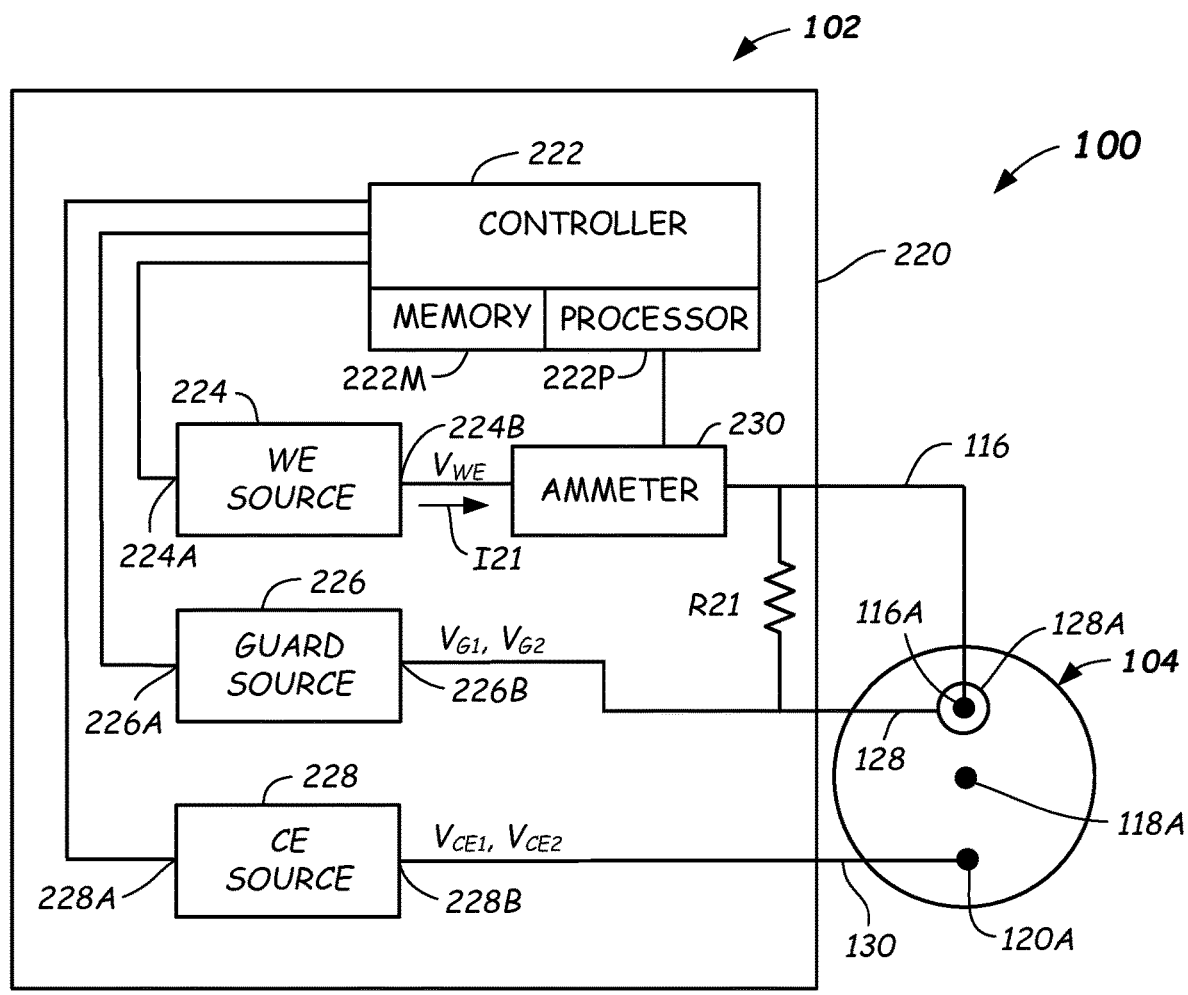
FIG. 2 schematically illustrates a portion of a glucose monitoring system including a glucose sensor according to one or more embodiments disclosed herein.

Additional reference is made to FIG. 2, which schematically illustrates an embodiment of a portion of the glucose monitoring system 100 provided herein. The glucose monitoring system 100 depicted in FIG. 2 may include the glucose transmitter 102 electrically coupled to the glucose sensor assembly 104. The glucose transmitter 102 may include an analog front end 220 that may be configured to electrically couple to components of the glucose sensor assembly 104.

The glucose transmitter 102 may include a controller 222 that is configured to control and monitor components within the glucose monitoring system 100 and/or the analog front end 220. The controller 222 may include a processor 222P coupled to a memory 222M. The memory 222M may have instructions stored therein that, when executed by the processor 222P, cause the controller 222 to control and/or monitor various components of the glucose monitoring system 100 as described herein.

Processor 222P may be, for example, a computational resource such as but not limited to a microprocessor, a microcontroller, an embedded microcontroller, a digital signal processor (DSP), a field programmable gate array (FPGA) configured to perform as a microcontroller, or the like. Memory 222M may be any suitable type of memory, such as but not limited to, one or more of a volatile memory and/or a non-volatile memory.

The analog front end 220 may also include a plurality of power sources that are configured to electrically couple to components of the glucose sensor assembly 104 and that may be controlled by the controller 222. For example, the power sources may bias components, such as the electrodes 117, 119 and 121, at different predetermined voltages. In the embodiment depicted in FIG. 2, the analog front end 220 may include three power sources, which are referred to individually as a working electrode (WE) source 224, a guard source 226, and a counter electrode (CE) source 228. The analog front end 220 may include other components that are not shown. For example, the analog front end 220 may include components that monitor a voltage of the reference electrode 119.

The WE source 224 may be configured to apply a working electrode voltage $V_{WE}$ to the working electrode contact region 116A of the glucose sensor assembly 104. The WE source 224 may include a control input 224A coupled to the controller 222 and an output 224B that applies the working electrode voltage $V_{WE}$ and supplies a current I21. For example, the controller 222 may transmit instructions to the WE source 224 via the control input 224A that cause the WE source 224 to output the working electrode voltage $V_{WE}$ via the output 224B.

The analog front end 220 may also include a current measurement circuit (e.g., an ammeter) 230 configured to measure the output current I21 of the WE source 224, which may be the current flowing to the working electrode 117. The ammeter 230 may generate signals indicating the amperage of the current I21 and may transmit these signals to the controller 222. In some embodiments, the memory 222M may include instructions, that when executed by the processor 222P, cause the controller 222 to generate a signal in response to the measured current flow of the ammeter 230 exceeding a predetermined (e.g., threshold) amperage or being outside a predetermined (e.g., threshold) range of amperages. For example, in some embodiments, the controller 222 may be configured to generate a signal in response to the current I21 measured by the ammeter 230 being greater than a first predetermined amperage or less than a second predetermined amperage. The signal generated by the controller 222 may indicate that an error condition exists with the glucose monitoring system 100.

The CE source 228 may be configured to provide two or more counter electrode voltages to the counter electrode contact region 120. The CE source 228 may include a control input 228A and an output 228B that outputs two or more counter electrode voltages. The control input 228A may be coupled to the controller 222 and may receive instructions as to voltages to output at the output 228B. The CE source 228 may be configured to output at least a first counter electrode (CE) voltage $V_{CE1}$ and a second CE voltage $V_{CE2}$ to the counter electrode 121. For example, the controller 222 may transmit instructions to the CE source 228 via the control input 228A that cause the CE source 228 to output at least one of the first CE voltage $V_{CE1}$ or the second CE voltage $V_{CE2}$.

In some embodiments, the CE source 228 may output the first CE voltage $V_{CE1}$ during normal operation of the glucose monitoring system 100. The CE source 228 may output the second CE voltage $V_{CE2}$ when the glucose monitoring system 100 is in an analytical (e.g., self-testing) state as described herein. In some embodiments, the first CE voltage $V_{CE1}$ is not equal to the working electrode voltage $V_{WE}$ and the second CE voltage $V_{CE2}$ is equal to the working electrode voltage $V_{WE}$. Other suitable voltages may be used.

The guard source 226 may be configured to apply one or more guard ring voltages to the guard ring 128. In the embodiment depicted in FIG. 2, the guard source 226 may be configured to output at least a first guard ring voltage $V_{G1}$ and a second guard ring voltage $V_{G2}$ to the guard ring 128. The guard source 226 may include a control input 226A coupled to the controller 222 and an output 226B configured to be electrically coupled to the guard ring 128. The output 226B may apply at least the first guard ring voltage $V_{G1}$ or the second guard ring voltage $V_{G2}$ to the guard ring 128. For example, the controller 222 may transmit instructions to the guard source 226 via the control input 226A that cause the guard source 226 to output at least one of the first guard ring voltage $V_{G1}$ or the second guard ring voltage $V_{G2}$ to the guard ring 128.

In some embodiments, the first guard ring voltage $V_{G1}$ may be equal to the working electrode voltage $V_{WE}$ and the second guard ring voltage $V_{G2}$ may not be equal to the working electrode voltage $V_{WE}$. Other suitable voltages may be used. In some embodiments, the guard source 226 may output the first guard ring voltage $V_{G1}$ when the glucose monitoring system 100 is in an operating state. The guard source 226 may output the second guard ring voltage $V_{G2}$ when the glucose monitoring system 100 is in an analytical state. In some embodiments, the output 226B of the guard source 226 may have low impedance to source or sink current (e.g., current I21) when the glucose monitoring system 100 is an analytical state as described herein.

A reference resistor R21 may be configured to be electrically coupled between the working electrode 117 (e.g., at working electrode contact region 116A and/or 116B) and the guard ring 128, for example. In some embodiments, the reference resistor R21 may be electrically coupled between an output of the ammeter 230 and the output 226B of the guard source 226. In some embodiments, the reference resistor R21 may have a high resistance value, such as, e.g., about 5 MΩ with a precision of 0.5 to 1%. The reference resistor R21 may have other suitable resistances and precision values. In some embodiments, the reference resistor R21 may be located in the glucose transmitter 102 and, in other embodiments, the reference resistor R21 may be located in the glucose sensor assembly 104 (e.g., as shown in glucose sensor assembly 704 of FIG. 7).

In some embodiments, the glucose monitoring system 100 may operate in at least an operational state, a first analytical state, and a second analytical state. When the glucose monitoring system 100 is in the operational state, the glucose monitoring system 100 measures glucose concentrations in the interstitial fluid 108 (FIG. 1A) as described herein. The concentration of glucose in the interstitial fluid 108 is proportional to the conductivity of the interstitial fluid 108. Therefore, glucose concentrations in the interstitial fluid 108 may be continuously measured by continuously measuring the current I21 flowing to the working electrode contact region 116A (e.g., under a constant bias). For example, the ammeter 230 may continuously measure the current I21. The current I21 may be equal to current flowing between the working electrode 117 and the counter electrode 121 plus the current flowing through the reference resistor R21. In normal operation wherein the glucose monitoring system 100 is monitoring glucose concentrations, the working electrode voltage $V_{WE}$ and the first guard ring voltage $V_{G1}$ may be equal, so no current flows through the reference resistor R21.

In all the states of the glucose monitoring system 100 and the glucose transmitter 102 described herein, the WE source 224 may apply the working electrode voltage $V_{WE}$ to the working electrode 117. For example, the controller 222 may send instructions to the WE source 224 that cause the WE source 224 to output the working electrode voltage $V_{WE}$ on the output 224B. In some embodiments, the working electrode voltage $V_{WE}$ may be about 1.5 v, although other suitable values may be used (e.g., greater than 1.5 volts, less than 1.5 volts, 1.0 volts, 0.5 volts, 0.1 volts, or the like). The output 224B of the WE source 224 may have low impedance to enable the WE source 224 to source and/or sink the current I21.

The glucose transmitter 102 may be in one or more analytical states to perform one or more self-tests or integrity checks. The glucose transmitter 102 may also be in an operational state or a normal state when the glucose transmitter 102 processes signals from the glucose sensor assembly 104 to measure glucose concentrations. Example states of the outputs of the WE source 224, the guard source 226, and the CE source 228 are summarized by relative values shown in Table 1. Example values of $V_{WE}$, $V_{CE1}$, $V_{CE2}$, $V_{G1}$, and $V_{G2}$ in the different states are shown in Table 2. Other suitable voltages may be used.

TABLE 1

Analytical states of the glucose transmitter 102.

| Operating State | Working Electrode Voltage | Counter Electrode Voltage | Guard Ring Voltage | Measured Current $I_{21}$ |
|---|---|---|---|---|
| Normal | $V_{WE}$ | $V_{CE1} \neq V_{WE}$ Counter electrode voltage not equal to working electrode voltage | $V_{G1} = V_{WE}$ Guard ring voltage equal to working electrode voltage | Dependent on glucose concentration |
| First Analytical State (first integrity check) | $V_{WE}$ | $V_{CE2} = V_{WE}$ Counter electrode voltage equal to working electrode voltage | $V_{G1} = V_{WE}$ Guard ring voltage equal to working electrode voltage | Ideally, no current flow |
| Second Analytical State (second integrity check) | $V_{WE}$ | $V_{CE2} = V_{WE}$ Counter electrode voltage equal to working electrode voltage | $V_{G2} \neq V_{WE}$ Guard ring voltage not equal to working electrode voltage | Ideally, only current flow is through R21 |

TABLE 2

Example values of $V_{WE}$, $V_{CE1}$, $V_{CE2}$, $V_{G1}$, and $V_{G2}$.

| Operating State | Working Electrode Voltage | CE Electrode Voltage | Guard ring Voltage | Measured Current |
|---|---|---|---|---|
| Normal | $V_{WE}$ = 1.5 v | $V_{CE1}$ = 1.0 v | $V_{G1}$ = 1.5 V | Dependent on glucose concentration |
| First analytical state | $V_{WE}$ = 1.5 v | $V_{CE2}$ = 1.5 v | $V_{G1}$ = 1.5 v | Ideally no current flow |
| Second analytical state | $V_{WE}$ = 1.5 v | $V_{CE2}$ = 1.5 v | $V_{G2}$ = 1.0 v | 100 nA when R21 = 5 MΩ |

Figure 3:
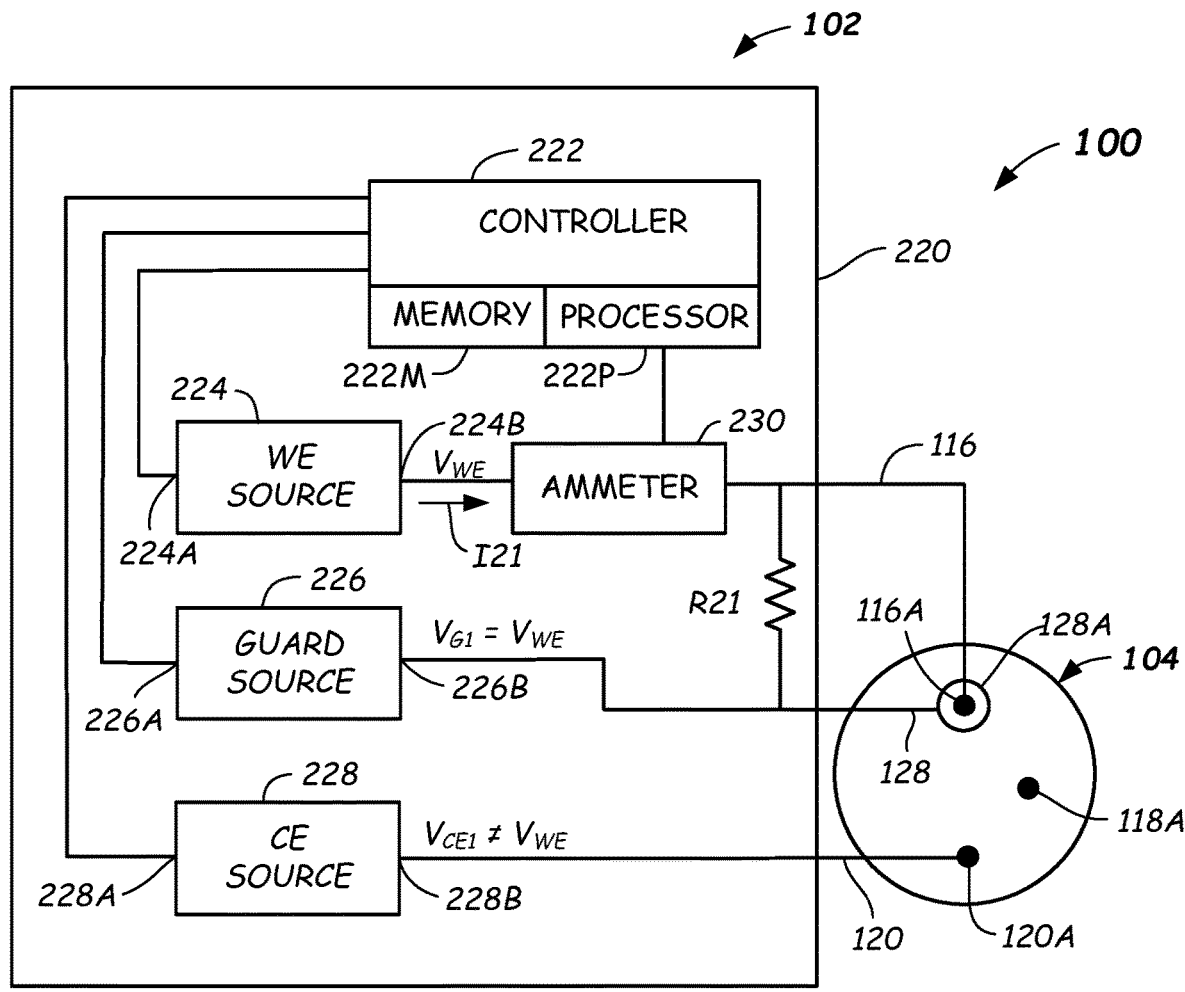
FIG. 3 schematically illustrates a portion of a glucose monitoring system, including a glucose sensor, in an operational state according to one or more embodiments disclosed herein.

Reference is now made to FIG. 3, which schematically illustrates an embodiment of the glucose monitoring system 100 configured in the operational state. When the glucose monitoring system 100 is in the operational state, the CE source 228 may apply the first CE voltage $V_{CE1}$ to the counter electrode contact region 120A. For example, the controller 222 may transmit instructions to the CE source 228 via the control input 228A that cause the CE source 228 to output the first CE voltage $V_{CE1}$ at the output 228B. The first CE voltage $V_{CE1}$ output by the CE source 228 when the glucose monitoring system 100 is in the operational state is not equal to the working electrode voltage $V_{WE}$. For example, the first counter voltage $V_{CE1}$ may be less than the working electrode voltage $V_{WE}$ or the first counter voltage $V_{CE1}$ may be greater than the working electrode voltage $V_{WE}$. Accordingly, current may flow between the working electrode 117 and the counter electrode 121. In some embodiments, the difference between the working electrode voltage $V_{WE}$ and the first counter voltage $V_{CE1}$ is about 0.5 v. In some embodiments, the working electrode voltage $V_{WE}$ is about 1.5 v and the first counter voltage $V_{CE1}$ is about 1.0 v. Other suitable voltages may be used.

When the glucose monitoring system 100 is in the operational state, the guard source 226 may apply the first guard ring voltage $V_{G1}$ to the guard ring 128. As described above, the first guard ring voltage $V_{G1}$ may be equal to the working electrode voltage $V_{WE}$. For example, the controller 222 may transmit instructions to the guard source 226 via the control input 226A that cause the guard source 226 to output the first guard ring voltage $V_{G1}$ at the output 226B. By setting the first guard ring voltage $V_{G1}$ equal to the working electrode voltage $V_{WE}$, no current flows between the guard ring 128 and the working electrode contact region 116A. Thus, the current flowing through the working electrode contact region 116A is the current flowing through the interstitial fluid 108 (FIG. 1A) and is proportional to the glucose concentration of the interstitial fluid 108. In such embodiments, the current flowing through the working electrode 117 is not affected by contaminants or the like on the surface 124 of glucose transmitter 102 or the surface of the substrate 110 (FIG. 1A).

In order to ensure accuracy, the glucose monitoring system 100 may perform periodic self-tests (e.g., integrity checks). Conventional glucose monitoring devices may include switches and the like for use during a self-test. The glucose monitoring system 100 described herein includes a reference resistor R21 that may be continuously electrically coupled between the working electrode contact region 116A and the guard ring 128. Therefore, the glucose monitoring system 100 described herein does not require additional switching circuitry.

Figure 4:
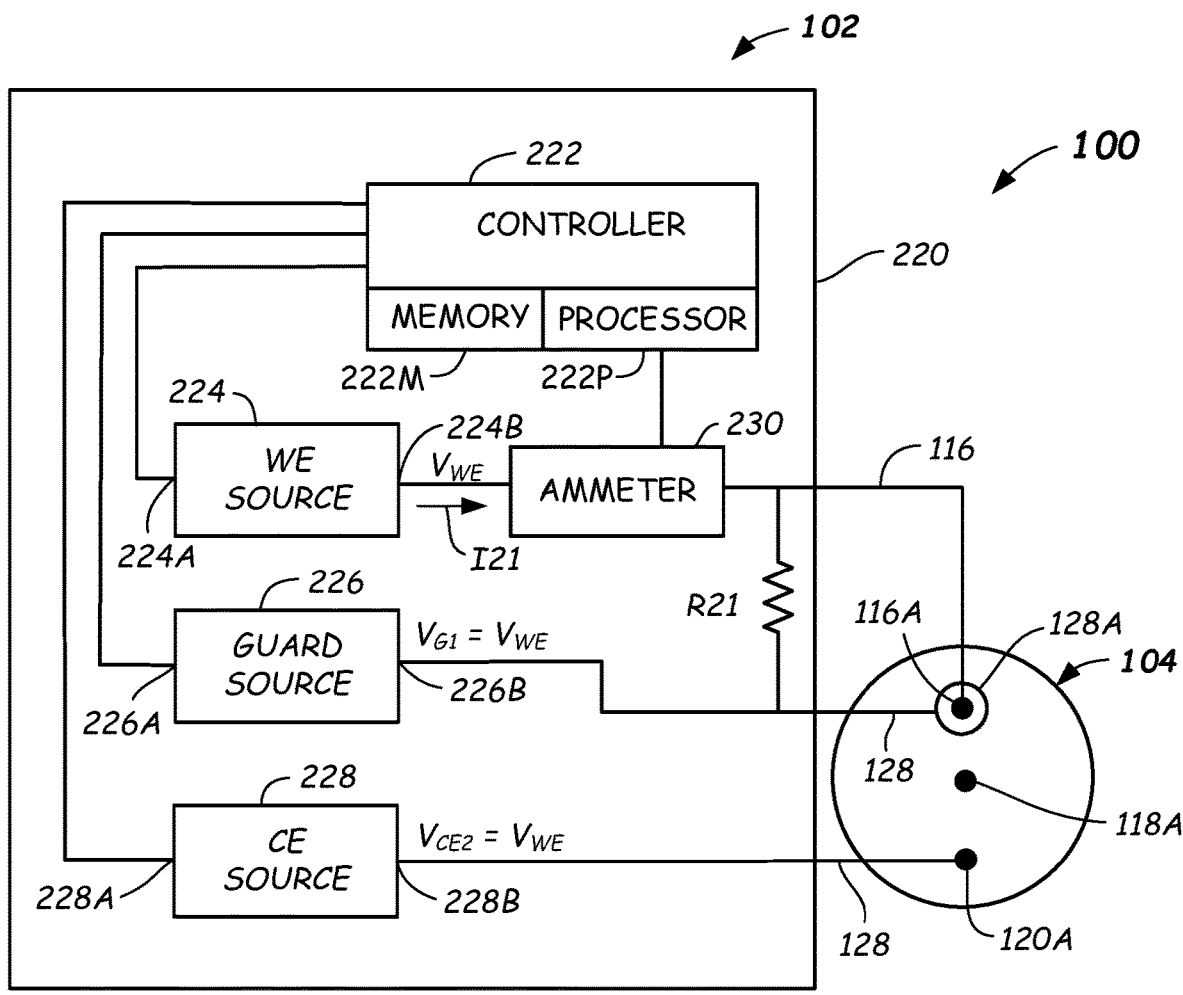
FIG. 4 schematically illustrates a portion of a glucose monitoring system, including a glucose sensor, in a first analytical state according to one or more embodiments disclosed herein.

Reference is now made to FIG. 4, which schematically illustrates an embodiment of the analog front end 220 configured in a first analytical state to perform a first integrity check. When the analog front end 220 is in the first analytical state, the voltages of the electrodes are set by the controller 222 to be the same. Thus, the WE source 224, the guard source 226, and the CE source 228 are instructed to output the same voltages such that $V_{WE}=V_{G1}=V_{CE2}$. In some embodiments, all the voltages may be set to 1.5 v. Because the voltages at the working electrode 117, the guard ring 128, and the counter electrode 121 are the same, no current is expected to flow between the electrodes. Thus, the ammeter 230 should not measure any current. The controller 222 may generate a signal indicating a fault in the glucose monitoring system 100 in response to the ammeter 230 measuring a current. In some embodiments, the controller 222 may generate a signal in response to the ammeter 230 measuring a current greater than a predetermined (e.g., threshold) amperage. In some embodiments, the predetermined amperage that causes the controller 222 to generate a signal (e.g., an error message, a fault signal and/or alarm) may be about 10-20 nanoamperes or greater, although other suitable values may be used. For example, some stray current associated with the components may flow wherein the stray current does not adversely affect the glucose monitoring system 100. In some embodiments, the predetermined amperage that causes the controller 222 to generate a signal may be set based on allowable errors and/or tolerances in the glucose monitoring system 100 (FIG. 1A).

Figure 5:
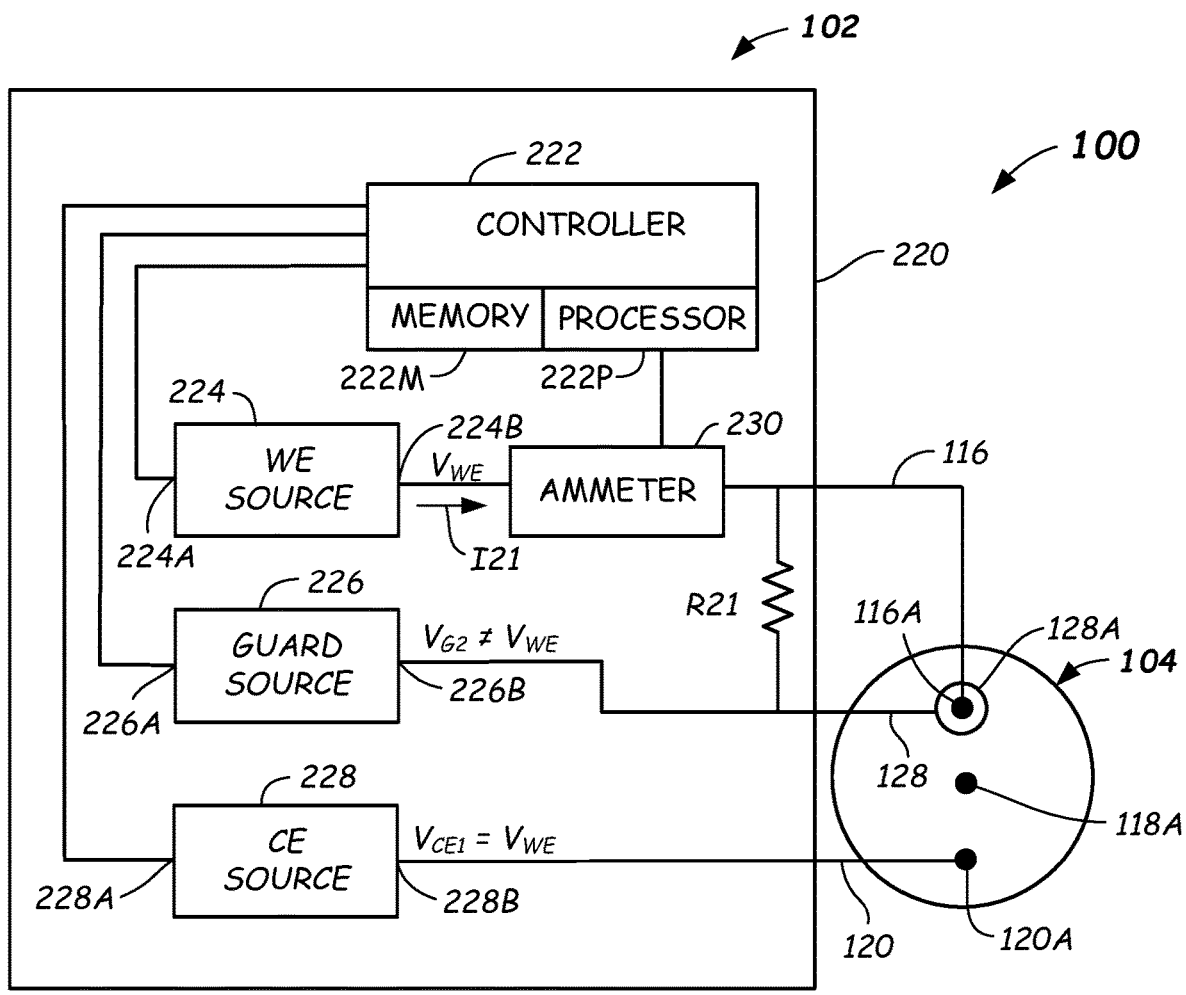
FIG. 5 schematically illustrates a portion of a glucose monitoring system, including a glucose sensor, in a second analytical state according to one or more embodiments disclosed herein.

Reference is now made to FIG. 5, which schematically illustrates an embodiment of the analog front end 220 configured in a second analytical state to perform a second integrity check. When the analog front end 220 is in the second analytical state, the voltages of all the electrodes are set by the controller 222 so that the current I21 is drawn through the reference resistor R21. For example, the second CE voltage $V_{CE2}$ may be equal to the working electrode voltage $V_{WE}$. The guard source 226 may be instructed to output the second guard ring voltage $V_{G2}$, which is not equal to the working electrode voltage $V_{WE}$. In some embodiments, the second guard ring voltage $V_{G2}$ is less than the working electrode voltage $V_{WE}$. For example, the working electrode voltage $V_{WE}$ may be 1.5 v and the second guard ring voltage $V_{G2}$ may be 1.0 v.

As described above, a voltage difference exists between the working electrode 117 and the guard ring 128 when the analog front end 220 is in the second analytical state. As shown in FIG. 5, this voltage difference is present across the reference resistor R21. The second CE voltage $V_{CE2}$ output by the CE source 228 is equal to the working electrode voltage $V_{WE}$ at the working electrode 117, so no current flows between the working electrode 117 and the counter electrode 121. If the glucose monitoring system 100 is operating correctly, the only current measured by the ammeter 230 is the current I21 flowing through the reference resistor R21. The reference resistor R21 may be a precision resistor and the working electrode voltage $V_{WE}$ and the second guard ring voltage $V_{G2}$ may be precise voltages, so that the precision of the resistance and the voltages are proportional to the accuracy of the second self-test performed by the glucose monitoring system 100. Under ideal conditions, the current measured by the ammeter 230 is equal to the voltage difference ($V_{WE}$-$V_{G2}$) divided by the resistance of the reference resistor R21.

The controller 222 may generate a signal (e.g., an error message, a fault signal and/or alarm) in response to the current measured by the ammeter 230 being greater than a first predetermined (e.g., threshold) amperage and/or less than a second predetermined (e.g., threshold) amperage during the second integrity test. For example, in some embodiments, the first predetermined amperage may be slightly greater (e.g., 2% greater, 5% greater, or the like) than current measured under ideal conditions, and the second predetermined amperage may be slightly less (e.g., 2% less, 5% less, or the like) than the current measured under ideal conditions. Other suitable predetermined amperage values may be used. The signal generated by the controller 222 may indicate a fault, such as contamination, with the glucose monitoring system 100.

Figure 6:
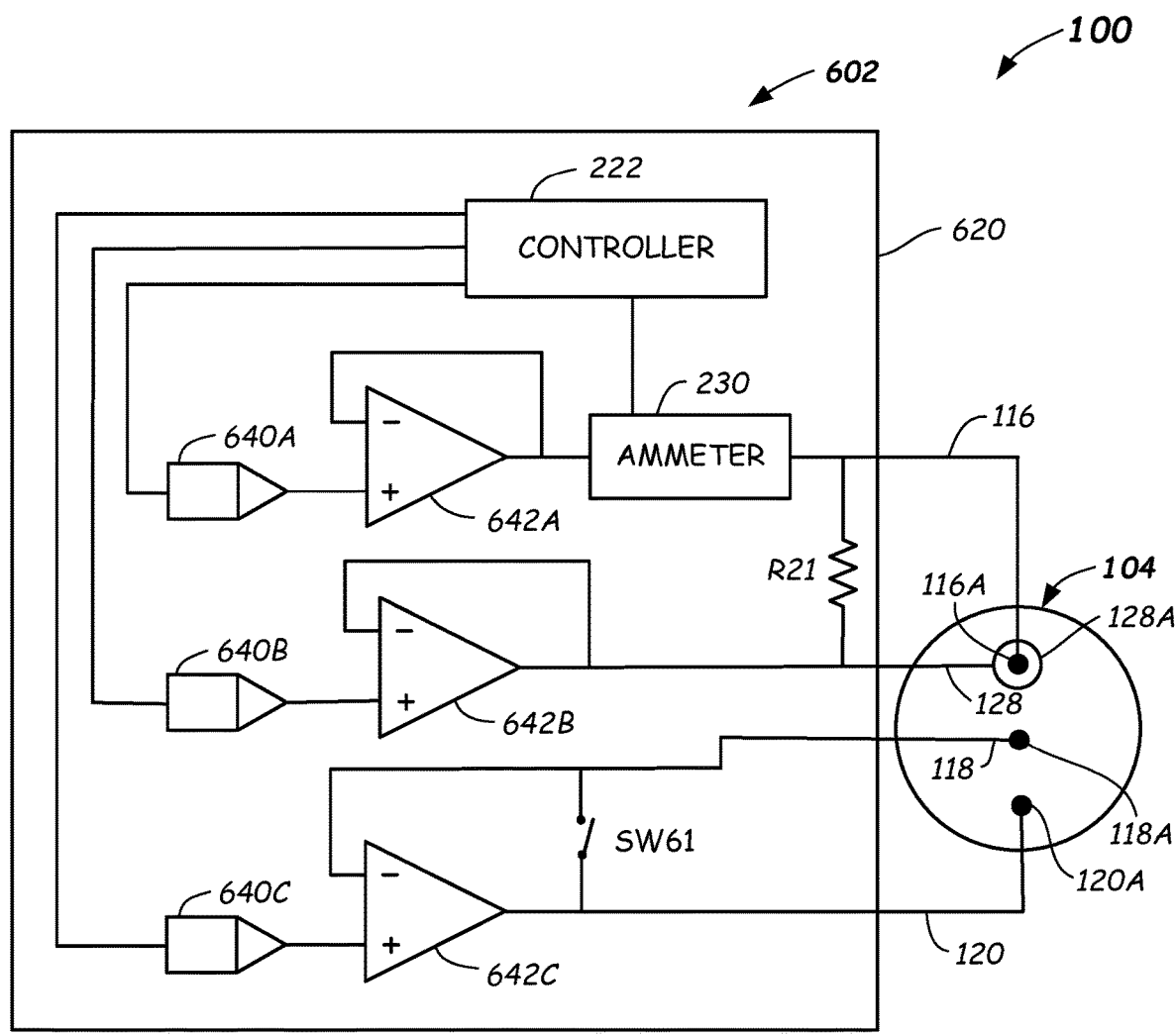
FIG. 6 schematically illustrates a portion of a glucose monitoring system including a glucose sensor according to one or more embodiments disclosed herein.

Reference is now made to FIG. 6, which schematically illustrates another embodiment of an analog front end 620 of the glucose monitoring system 100. The analog front end 620 may include digital-to-analog converters (DACs) coupled to the controller 222, wherein the DACs output the above-described voltages to the glucose sensor assembly 104. For example, the controller 222 may output digital (e.g., binary) values representative of the voltages the individual DACs are to output.

Figure 7:
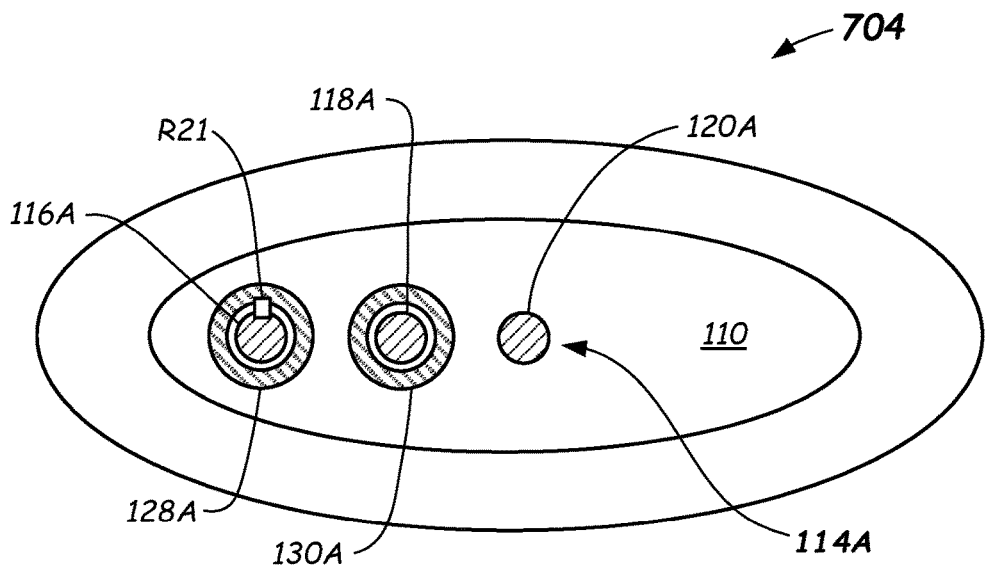
FIG. 7 illustrates a plan view of a glucose sensor with a resistor connected between a working electrode and a guard ring according to one or more embodiments disclosed herein.

The analog front end 620 depicted in FIG. 6 may include a first DAC 640A having a digital input coupled to the controller 222. An analog output of the first DAC 640A may be coupled to a non-inverting input of a first operational amplifier 642A that may be configured as a buffer. The output of the first operational amplifier 642A may be configured to couple to the working electrode contact region 116. The analog front end 620 may also include a second DAC 640B having a digital input coupled to the controller 222. An analog output of the second DAC 640B may be coupled to a non-inverting input of a second operational amplifier 642B. The output of the second operational amplifier 642B may be configured to couple to the guard ring 128. The second operational amplifier 642B may be configured as a buffer. The analog front end 620 may also include the reference resistor R21 coupled between an output of the ammeter 230 and an output of the second operational amplifier 642B. In some embodiments, the reference resistor R21 may be located in the glucose sensor assembly 104 as shown in FIG. 7.

The analog front end 620 may further include a third DAC 640C having a digital input coupled to the controller 222. An analog output of the third DAC 640C may be coupled to the non-inverting input of a third operational amplifier 642C that may be configured as a buffer. In some embodiments, the counter electrode contact region 120 and the reference electrode contact region 118 may be coupled together by a switch SW61 that may be controlled by the controller 222. The controller 222 may close the switch SW61 when the analog front end 620 is in an analytical state and the controller 222 may open the switch SW61 when the analog front end 620 is in a normal operating state. When the glucose transmitter 602 is in an analytical state, the switch SW61 may close, which applies the counter electrode voltage as a reference electrode voltage. The switch SW61 may open when the glucose transmitter 602 is in normal operation measuring glucose concentrations. In some embodiments, a similar switching mechanism (not shown) may be included in the glucose transmitter 102 of FIGS. 2-5.

The analog front end 620 may operate in the same manner as the analog front end 220 (FIGS. 2-5). For example, the analog front end 620 may output the voltages $V_{WE}$, $V_{CE1}$, $V_{CE2}$, $V_{G1}$, and $V_{G2}$ depending on the state of the analog front end 620 and/or the glucose transmitter 602.

In some embodiments, the reference resistor R21 may be located on or in the glucose sensor assembly 104. Reference is made to FIG. 7, which illustrates a plan view of a glucose sensor assembly 704 with the reference resistor R21 located thereon. The reference resistor R21 may be electrically connected between the working electrode contact region 116 and the guard ring 128, for example. The reference resistor R21 alternatively may be coupled directly between the working electrode 117 and the guard ring 128 in other embodiments. The glucose transmitter 102 (FIG. 1A) may electrically couple to the glucose sensor assembly 704 and function as described herein.

Figure 8:
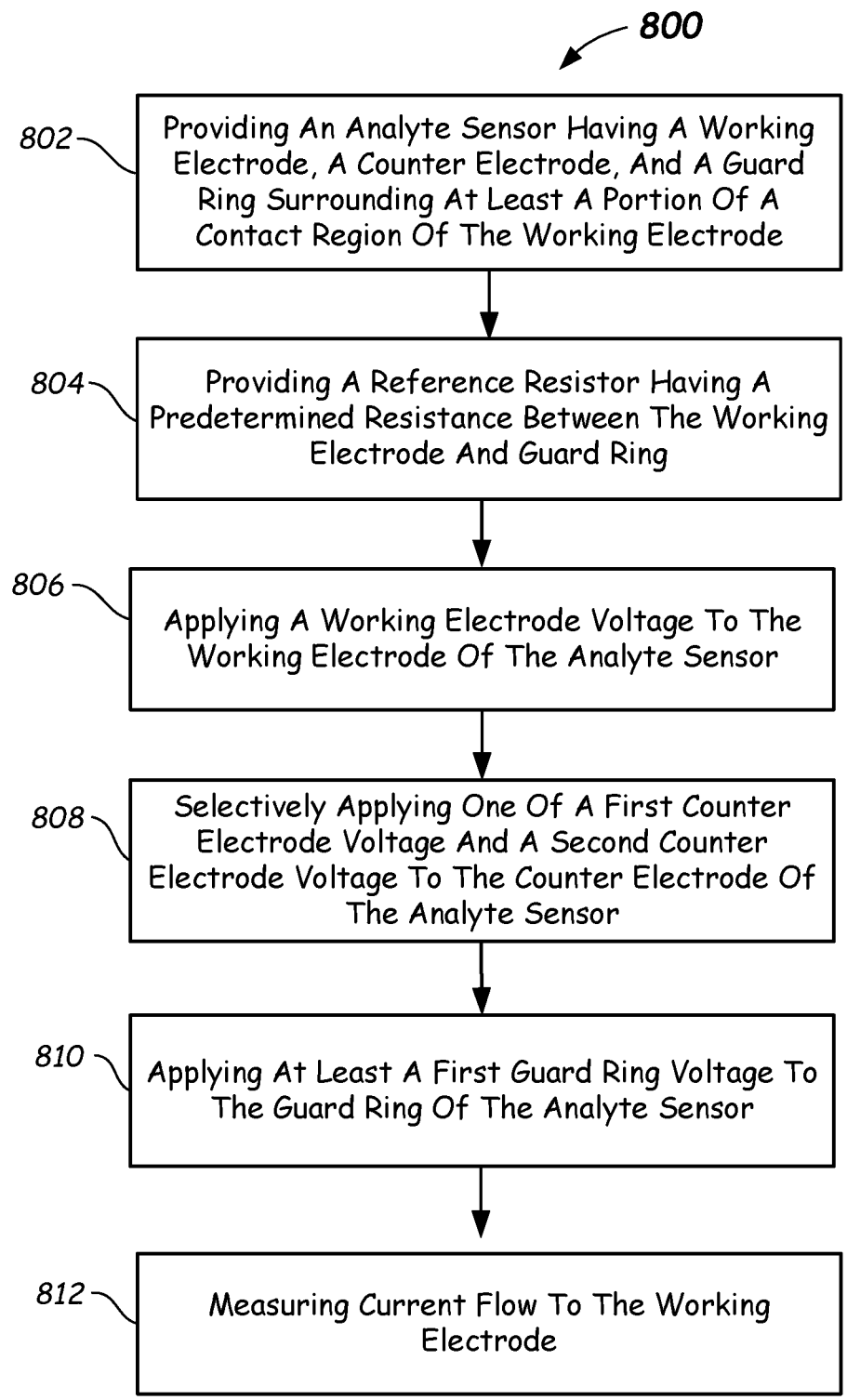
FIG. 8 illustrates a flowchart of a method of operating a glucose monitoring system according to one or more embodiments disclosed herein.

Reference is now made to FIG. 8, which illustrates a flowchart 800 that depicts a method of operating an analyte monitoring system (e.g., glucose monitoring system 100) in accordance with embodiments provided herein. The method includes, at 802, providing an analyte sensor (e.g., glucose sensor assembly 104 or 704) having a working electrode (e.g., working electrode 117), a counter electrode (e.g., counter electrode 121), and a guard ring (e.g., guard ring 128) surrounding at least a portion of the working electrode contact region. The method includes, at 804, providing a reference resistor (e.g., reference resistor R21) electrically coupled between the working electrode and guard ring of the analyte sensor. The method includes, at 806, applying a working electrode voltage (e.g., working electrode voltage $V_{WE}$) to the working electrode of the analyte sensor. The method includes, in 808, selectively applying one of a first counter electrode voltage (e.g., first CE voltage $V_{CE1}$) and a second counter electrode voltage (e.g., second CE voltage $V_{CE2}$) to the counter electrode of the analyte sensor. The method includes, at 810, applying at least a first guard ring voltage (e.g., first guard ring voltage $V_{G1}$) to the guard ring of the analyte sensor. The method includes, at 812, measuring current flow to the working electrode.

In some embodiments, the first counter electrode voltage $V_{CE1}$ and the first guard ring voltage $V_{G1}$ may be the same as the working electrode voltage $V_{WE}$. In other embodiments, the first guard ring voltage $V_{G1}$ may be different than the working electrode voltage $V_{WE}$. Current flow to the working electrode 117 may be measured to determine if the glucose monitoring system 100 is functioning properly (e.g., if the current flow is as expected based on the voltages applied to the working electrode 117, counter electrode 121, guard ring 128 and/or reference electrode 119).

In some embodiments, the reference electrode contact regions 118A/118B may include a guard ring 130 that at least partially surrounds the reference electrode contact regions 118A/118B.

While the disclosure is susceptible to various modifications and alternative forms, specific assembly and apparatus embodiments and methods thereof have been shown by way of example in the drawings and are described in detail herein. It should be understood, however, that the invention is not limited to the particular assemblies, apparatus, or methods disclosed herein but, to the contrary, the invention covers all modifications, equivalents, and alternatives falling within the scope of the claims.

What is claimed is:

1. An analyte monitor, comprising:
   a working electrode voltage source configured to provide a working electrode voltage to a working electrode;
   a counter electrode voltage source configured to provide one or more counter electrode voltages to a counter electrode;
   a guard ring voltage source configured to provide a guard ring voltage to a guard ring;
   a current measurement circuit configured to measure current flow from the working electrode voltage source to the working electrode; and
   a controller including at least one processor coupled to a memory, the memory including instructions stored therein that, when executed by the at least one processor, perform at least one integrity check comprising:
      providing a first instruction to the working electrode voltage source to provide the working electrode voltage to the working electrode of an analyte sensor;
      providing a second instruction to the counter electrode voltage source to provide a first counter electrode voltage or a second counter electrode voltage to the counter electrode of the analyte sensor,
      providing a third instruction to the guard ring voltage source to provide the guard ring voltage to the guard ring that at least partially surrounds a contact region of the working electrode,
      wherein the working electrode voltage source, the counter electrode voltage source, and the guard ring voltage source are separate and distinct voltage sources;
      measuring the current flow by the current measurement circuit; and
      determining that the analyte monitor is faulty based on the current flow.

2. The analyte monitor of claim 1, wherein the memory further comprises instructions that, when executed by the at least one processor, cause the controller to measure an analyte concentration by:
   applying the working electrode voltage to the working electrode,
   applying the first counter electrode voltage to the counter electrode, wherein the first counter electrode voltage is independent of and not equal to the working electrode voltage, and
   applying the guard ring voltage to the guard ring, wherein the guard ring voltage is independent of and equal to the working electrode voltage.

3. The analyte monitor of claim 2, wherein the memory further comprises instructions that, when executed by the at least one processor, cause the controller to generate a signal in response to measured current flow to the working electrode exceeding a predetermined amperage during measurement of the analyte concentration.

4. The analyte monitor of claim 1, wherein the memory further comprises instructions that, when executed by the at least one processor, cause the controller to perform a first integrity check by:
   applying the working electrode voltage to the working electrode,
   applying the second counter electrode voltage to the counter electrode, wherein the second counter electrode voltage is equal to the working electrode voltage, and
   applying the guard ring voltage to the guard ring, wherein the guard ring voltage is equal to the working electrode voltage.

5. The analyte monitor of claim 4, wherein the memory further comprises instructions that, when executed by the at least one processor, cause the controller to generate a signal in response to measured current flow to the working electrode exceeding a predetermined amperage during the first integrity check.

6. The analyte monitor of claim 5, wherein the predetermined amperage is greater than 20 nanoamperes during the first integrity check.

7. The analyte monitor of claim 4, wherein the memory further comprises instructions that, when executed by the at least one processor, cause the controller to apply a reference electrode voltage equal to the second counter electrode voltage to a reference electrode of the analyte sensor during the first integrity check.

8. The analyte monitor of claim 1, wherein:
   the memory further comprises instructions that, when executed by the at least one processor, cause the controller to;
   selectively provide a first guard ring voltage and a second guard ring voltage to the guard ring;
   the memory further comprises instructions that, when executed by the at least one processor, cause the controller to perform the at least one integrity check by:
      applying the second counter electrode voltage to the counter electrode, wherein the second counter electrode voltage is equal to the working electrode voltage, and applying the second guard ring voltage to the guard ring, wherein the second guard ring voltage is not equal to the working electrode voltage.

9. The analyte monitor of claim 8, wherein the memory further comprises instructions that, when executed by the at least one processor, cause the controller to generate a signal in response to the measured current flow to the working electrode exceeding a first predetermined amperage or being less than a second predetermined amperage during the at least one integrity check.

10. The analyte monitor of claim 9, wherein the first predetermined amperage is at least 2% greater than a difference between the working electrode voltage and the second guard ring voltage divided by a resistance of a reference resistor, and the second predetermined amperage is at least 2% less than a difference between the working electrode voltage and the second guard ring voltage divided by the resistance of the reference resistor during the at least one integrity check.

11. The analyte monitor of claim 8, wherein the memory further comprises instructions that, when executed by the at least one processor, cause the controller to apply a reference electrode voltage equal to the second counter electrode voltage to a reference electrode of the analyte sensor during the at least one integrity check.

12. An analyte monitoring system, comprising:
an analyte sensor having a working electrode and a counter electrode;
a guard ring surrounding at least a portion of a contact region of the working electrode;
a reference resistor electrically coupled between the working electrode and the guard ring; and
an analyte transmitter coupled to the analyte sensor, the analyte transmitter including:
a working electrode voltage source;
a counter electrode voltage source;
a guard ring voltage source;
a current measurement circuit configured to measure current flow from the working electrode voltage source to the working electrode; and
a controller including at least one processor coupled to a memory, the memory having instructions stored therein that, when executed by the at least one processor, perform at least one integrity check comprising:
providing a first instruction to the working electrode voltage source to provide a working electrode voltage to the working electrode;
providing a second instruction to the counter electrode voltage source to selectively provide a first counter electrode voltage and a second counter electrode voltage to the counter electrode,
wherein the first counter electrode voltage is indicative of an analyte monitoring mode of the analyte monitor and the second counter electrode voltage is indicative of an integrity check of the analyte monitor;
providing a third instruction to the guard ring voltage source to provide a guard ring voltage to the guard ring,
wherein the working electrode voltage source, the counter electrode voltage source, and the guard ring voltage source are separate and distinct voltage sources;
measuring the current flow by the current measurement circuit; and
determining that the analyte monitor is faulty based on the current flow.

13. The analyte monitoring system of claim 12, wherein the memory further comprises instructions that, when executed by the at least one processor, cause the controller to measure an analyte concentration by:
applying the working electrode voltage to the working electrode,
applying the first counter electrode voltage to the counter electrode,
wherein the first counter electrode voltage is not equal to the working electrode voltage, and
applying the guard ring voltage to the guard ring, wherein the guard ring voltage is equal to the working electrode voltage.

14. The analyte monitoring system of claim 13, wherein the memory further comprises instructions that, when executed by the at least one processor, cause the controller to generate a signal in response to measured current flow to the working electrode exceeding a predetermined amperage during measurement of the analyte concentration.

15. The analyte monitoring system of claim 13, wherein the memory further comprises instructions that, when executed by the at least one processor, cause the controller to perform a first integrity check by:
applying the working electrode voltage to the working electrode,
applying the second counter electrode voltage to the counter electrode,
wherein the second counter electrode voltage is equal to the working electrode voltage, and
applying the guard ring voltage to the guard ring, wherein the guard ring voltage is equal to the working electrode voltage.

16. The analyte monitoring system of claim 15, wherein the memory further comprises instructions that, when executed by the at least one processor, cause the controller to generate a signal in response to measured current flow to the working electrode exceeding a predetermined amperage during the first integrity check.

17. The analyte monitoring system of claim 16, wherein the predetermined amperage is greater than 20.0 nanoamperes.

18. The analyte monitoring system of claim 15, wherein the analyte sensor has a reference electrode, and wherein the memory further comprises instructions that, when executed by the at least one processor, cause the controller to apply a reference electrode voltage equal to the second counter electrode voltage to the reference electrode during the first integrity check.

19. The analyte monitoring system of claim 13, wherein:
the memory has instructions stored therein that, when executed by the at least one processor, cause the controller to:
selectively provide a first guard ring voltage and a second guard ring voltage to the guard ring; and
perform the at least one integrity check by:
applying the second counter electrode voltage to the counter electrode, wherein the second counter electrode voltage is equal to the working electrode voltage, and
applying the second guard ring voltage to the guard ring, wherein the second guard ring voltage is not equal to the working electrode voltage.

20. The analyte monitoring system of claim 19, wherein the memory further comprises instructions that, when executed by the at least one processor, cause the controller to generate a signal in response to measured current flow to the working electrode exceeding a first predetermined amperage or being less than a second predetermined amperage during the at least one integrity check.

21. The analyte monitoring system of claim 20, wherein the first predetermined amperage is at least 2% greater than a difference between the working electrode voltage and the second guard ring voltage divided by a resistance of the reference resistor, and the second predetermined amperage is at least 2% less than a difference between the working electrode voltage and the second guard ring voltage divided by the resistance of the reference resistor during the at least one integrity check.

22. The analyte monitoring system of claim 19, wherein the analyte sensor has a reference electrode, and wherein the memory further comprises instructions that, when executed by the at least one processor, cause the controller to apply a reference electrode voltage equal to the first counter electrode voltage to the reference electrode during the at least one integrity check.

23. A method of operating an analyte monitoring system, comprising:
providing an analyte sensor having a working electrode and a counter electrode;
providing a guard ring surrounding at least a portion of a contact region of the working electrode;
providing a reference resistor coupled between the working electrode and the guard ring;
providing a first instruction, by at least one processor, to a working electrode voltage source to apply a working electrode voltage to the working electrode;
providing a second instruction, by the at least one processor, to a counter electrode power source to apply one of a first counter electrode voltage or a second counter electrode voltage to the counter electrode;
providing a third instruction, by the at least one processor, to a counter electrode voltage source to apply at least a first guard ring voltage to the guard ring from a guard ring voltage source,
wherein the working electrode voltage source, the counter electrode voltage source, and the guard ring voltage source are separate and distinct voltage sources; and
measuring current flow to the working electrode by an ammeter disposed between the working electrode voltage source and the working electrode.

24. The method of claim 23, further comprising measuring an analyte concentration by:
applying the first counter electrode voltage to the counter electrode, wherein the first counter electrode voltage is not equal to the working electrode voltage, and
applying the first guard ring voltage to the guard ring, wherein the first guard ring voltage is equal to the working electrode voltage.

25. The method of claim 23, further comprising performing a first integrity check by:
applying the second counter electrode voltage to the counter electrode, and
applying the first guard ring voltage to the guard ring,
wherein the second counter electrode voltage and the first guard ring voltage are equal to the working electrode voltage.

26. The method of claim 23, further comprising performing a second integrity check by:
applying the second counter electrode voltage to the counter electrode, wherein the second counter electrode voltage is equal to the working electrode voltage, and
applying a second guard ring voltage to the guard ring, wherein the second guard ring voltage is not equal to the working electrode voltage.

* * * * *